(12) United States Patent
Valencia (10) Patent No.: US 8,323,325 B2
(45) Date of Patent: Dec. 4, 2012

(54) BALLOON WITH WINGS FOR ROTATIONAL STENT

(75) Inventor: Hans Valencia, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1701 days.

(21) Appl. No.: 11/526,326

(22) Filed: Sep. 25, 2006

(65) Prior Publication Data

US 2008/0077224 A1 Mar. 27, 2008

(51) Int. Cl.
*A61F 2/06* (2006.01)
(52) U.S. Cl. ........................................ 623/1.11
(58) Field of Classification Search .................. 623/1.11; 606/191, 192, 194, 195; 604/96, 104
See application file for complete search history.

(56) References Cited

U.S. PATENT DOCUMENTS

| | | | |
|---|---|---|---|
| 4,917,088 A | 4/1990 | Crittenden | 606/194 |
| 5,037,392 A | 8/1991 | Hillstead | 604/96 |
| 5,104,376 A | 4/1992 | Crittenden | 604/92 |
| 5,141,494 A | 8/1992 | Danforth et al. | 604/96 |
| 5,201,754 A | 4/1993 | Crittenden et al. | 606/194 |
| 5,639,274 A | 6/1997 | Fischell et al. | 604/96 |
| 5,730,698 A | 3/1998 | Fischell et al. | 600/3 |
| 5,935,135 A | 8/1999 | Bramfitt | |
| 5,954,740 A | 9/1999 | Ravenscroft et al. | 606/194 |
| 6,013,055 A | 1/2000 | Bampos et al. | 604/96 |
| 6,033,380 A | 3/2000 | Butaric et al. | 604/96 |
| 6,048,350 A * | 4/2000 | Vrba | 623/1.11 |
| 6,066,169 A * | 5/2000 | McGuinness | 623/1.16 |
| 6,258,099 B1 | 7/2001 | Mareiro et al. | 606/108 |
| 6,296,655 B1 | 10/2001 | Gaudoin et al. | 606/194 |
| 6,312,459 B1 * | 11/2001 | Huang et al. | 623/1.15 |
| 6,428,568 B2 | 8/2002 | Gaudoin et al. | 623/1.11 |
| 6,478,807 B1 * | 11/2002 | Foreman et al. | 606/194 |
| 6,494,906 B1 * | 12/2002 | Owens | 623/1.11 |
| 6,520,984 B1 * | 2/2003 | Garrison et al. | 623/1.11 |
| 6,533,807 B2 * | 3/2003 | Wolinsky et al. | 623/1.15 |
| 6,620,191 B1 | 9/2003 | Svensson | |
| 6,695,863 B1 | 2/2004 | Ramzipoor et al. | 606/194 |
| 6,988,881 B2 | 1/2006 | Motsenbocker et al. | 425/392 |
| 7,018,403 B1 * | 3/2006 | Pienknagura | 623/1.15 |
| 7,160,317 B2 | 1/2007 | McHale et al. | 623/1.11 |
| 7,195,638 B1 | 3/2007 | Sridharan | 606/194 |
| 7,235,093 B2 * | 6/2007 | Gregorich | 623/1.11 |
| 7,241,308 B2 * | 7/2007 | Andreas et al. | 623/1.11 |
| 7,473,271 B2 * | 1/2009 | Gunderson | 623/1.12 |
| 2002/0010489 A1 | 1/2002 | Grayzel | |
| 2002/0120321 A1 * | 8/2002 | Gunderson et al. | 623/1.11 |
| 2002/0163104 A1 | 11/2002 | Motsenbocker et al. | 264/320 |
| 2003/0004535 A1 * | 1/2003 | Musbach et al. | 606/194 |

(Continued)

*Primary Examiner* — Gary Jackson
*Assistant Examiner* — L. Bachman
(74) *Attorney, Agent, or Firm* — Vidas, Arrett & Steinkraus, P.A.

(57) ABSTRACT

The present invention provides a catheter system which includes a catheter, an expandable balloon, at least one securement member, and a stent. The stent is disposed about the catheter and comprises at least one undulating band that extends circumferentially around the longitudinal axis of the catheter system. The undulating band includes interconnected strut members which form a series of alternating peaks and valleys. Adjacent strut members comprise a strut pair, wherein each strut member of the strut pair includes a protuberance positioned along the length of the strut member, between a peak and a valley. The protuberances, which are substantially circumferentially opposed to one another, engage a securement member, thereby minimizing lateral stent movement on the delivery system during delivery.

15 Claims, 5 Drawing Sheets

U.S. PATENT DOCUMENTS

| | | | |
|---|---|---|---|
| 2003/0130717 A1 | 7/2003 | Hale et al. | 623/1.11 |
| 2003/0163157 A1 | 8/2003 | McMorrow et al. | 606/194 |
| 2003/0236563 A1* | 12/2003 | Fifer | 623/1.11 |
| 2004/0204749 A1* | 10/2004 | Gunderson | 623/1.12 |
| 2004/0215227 A1 | 10/2004 | McMorrow et al. | 606/191 |
| 2004/0249401 A1 | 12/2004 | Rabiner et al. | 606/159 |
| 2005/0010278 A1 | 1/2005 | Vardi et al. | 623/1.15 |
| 2005/0209674 A1 | 9/2005 | Kutscher et al. | 623/1.11 |
| 2005/0244533 A1 | 11/2005 | Motsenbocker et al. | 425/392 |
| 2005/0256410 A1 | 11/2005 | Rabiner et al. | 600/470 |
| 2005/0275140 A1 | 12/2005 | Motsenbocker et al. | 264/320 |
| 2005/0277877 A1 | 12/2005 | Motsenbocker et al. | 604/103.1 |

* cited by examiner

BALLOON WITH WINGS FOR ROTATIONAL STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments, this invention relates to implantable medical devices, their manufacture, and methods of use. Some embodiments are directed to delivery systems, such as catheter systems of all types, which are utilized in the delivery of such devices.

2. Description of the Related Art

Percutaneous transluminal coronary angioplasty (PTCA) is a procedure, which is well established for the treatment of blockages, lesions, stenosis, thrombus, etc. present in body lumens, such as the coronary and peripheral arteries and other vessels.

A widely used form of angioplasty makes use of a dilatation balloon catheter, which is introduced into and advanced through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents are not wholly satisfactory for use where the site of desired application of the stent is juxtaposed or extends across a bifurcation in an artery or vein such, for example, as the bifurcation in the mammalian aortic artery into the common iliac arteries. An example of a bifurcated stent apparatus is described in U.S. Patent Application Number 2005/0010278, the entire contents of which are incorporated herein by reference.

A stent is often delivered to the site on a balloon. It is necessary to position the stent at a precise location within a body lumen. This precision is difficult to achieve because slippage may occur between the stent and balloon during insertion of the stent and balloon combination. To facilitate the proper positioning of a stent, it is desirable to prevent any unwanted relative movement between the stent and the balloon. That is, it is desirable to improve device retention on a delivery system.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below. A brief abstract of the technical disclosure in the specification is provided as well.

BRIEF SUMMARY OF THE INVENTION

Embodiments of the invention contemplate an apparatus that improves stent retention on a delivery system. Some embodiments utilize securement members on the delivery system and protuberances on the stent. During advancement, the protuberances on the stent are engaged with the securement members to minimize longitudinal motion by the stent while on the delivery system.

At least one embodiment of the present invention includes a stent, catheter shaft, and balloon, where the stent is securely engaged to the balloon, such as described in U.S. Pat. No. 6,258,099, the entire contents of which being incorporated herein by reference.

In at least one embodiment, a catheter system comprises a catheter, at least one securement member, a balloon, and a stent. The balloon is disposed about the catheter, and the stent is disposed about the balloon. In some embodiments, the securement members are attached to the balloon at engagement regions. In other embodiments the securement members are attached to the catheter, specifically the catheter shaft, at engagement regions.

An engagement region is the area on the balloon or catheter shaft where at least a portion of the securement member is attached. That is, the securement member is fastened to the balloon or catheter shaft at the engagement region.

In some embodiments, the securement member resembles a "fin". In an embodiment, at least one of the securement members is attached to the balloon. A stent is disposed about the balloon, and the securement member.

The stent, having a longitudinal axis, comprises at least one undulating band made up of interconnected strut members and is disposed about the catheter. The interconnected strut members form a series of alternating peaks and valleys. Two immediately adjacent strut members comprise a strut pair with each strut member of the strut pair comprising at least one protuberance. The protuberances are positioned along the length of the strut members, between a peak and a valley, such that the protuberances are substantially circumferentially opposed to one another. The securement member is engaged by the protuberances of the strut pair, thereby securing the stent to the catheter system. In some embodiments there are a plurality of strut pairs and a plurality of securement members.

In some embodiments the catheter system comprises a plurality of securement members positioned circumferentially, longitudinally, or a combination of both, about the balloon.

Rather than having securement members resembling "fins," some embodiments provide securement members that could be referred to as "wings". In some embodiments, the "wings" attach to the cone of the balloon (the tapered region between the end of the balloon and the balloon's main body) at engagement regions and engage the protuberances on the stent. In other embodiments, the "wings" attach to the catheter shaft. There may be a single "wing" or a plurality.

BRIEF DESCRIPTION OF THE DRAWINGS

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Figure 1:
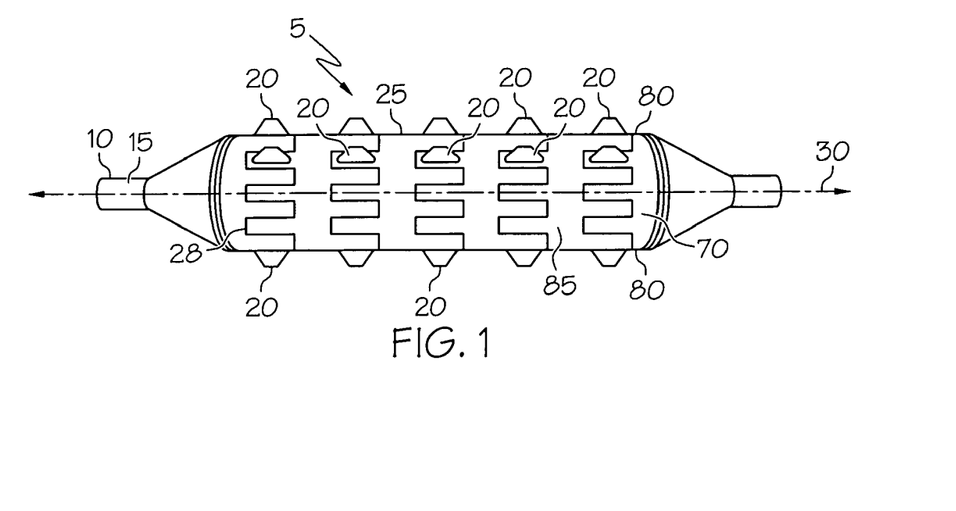
FIG. 1 is a side view of an embodiment of the invention, comprising securement members and a stent.

Referring now to the drawings, which are intended to illustrate embodiments of the invention only and not for the purpose of limiting same, in at least one embodiment of the invention, as shown in FIG. 1, a catheter system, shown generally at 5, comprises a catheter 10 with catheter shaft 15, and at least one securement member 20. As shown in FIG. 1, at least a portion of securement member 20 is engaged to an engagement region 25. The catheter system further includes a stent 28, shown generally in FIG. 1 and in greater detail in FIG. 2. FIG. 1 shows stent 28 disposed about catheter 10 and having a longitudinal axis 30. It should be noted that it is envisioned that the present invention can be adapted for use with all stents, including but not limited, to bifurcated stents.

Figure 2:
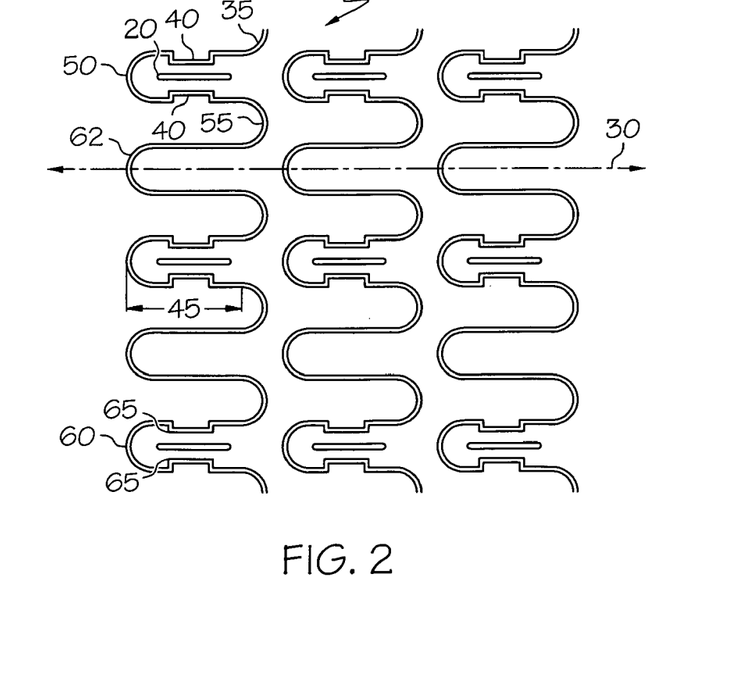
FIG. 2 is a top view of the stent of FIG. 1, in an unrolled state, with protuberances, and placed upon a region with securement members.

FIG. 2 depicts a portion of unrolled stent 28 comprised of at least one undulating band 35 extending circumferentially about longitudinal axis 30. Undulating band 35 is comprised of a plurality of interconnected strut members 40; each strut member has a length 45. Undulating band 35 is defined by a series of alternating peaks 50 and valleys 55. Also, immediately adjacent strut members 40 comprise a strut pair 60.

Figure 3:
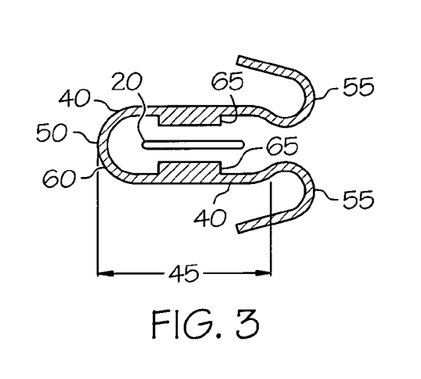
FIG. 3 is a top view of a portion of the stent shown in FIG. 2, in an expanded state.
Figure 4:
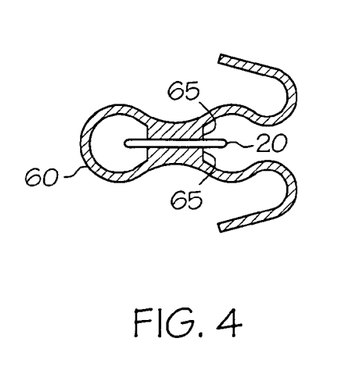
FIG. 4 is a top view of a portion of the stent shown in FIG. 2 and in FIG. 3, in an unexpanded state, with protuberances engaged to a securement member.

FIG. 3 shows a strut pair 60, and depicts each strut member 40 with at least one protuberance 65 along strut member length 45 and between peak 50 and valley 55. As seen in FIGS. 2 and 3, the protuberances 65 are substantially circumferentially opposed to one another. As seen in FIG. 3, the thickness of the portion of the strut member comprising protuberance 65 is greater than the thickness of the adjacent regions of the strut member 40. At least one securement member 20 is engaged by the substantially circumferentially opposed protuberances 65 of strut pair 60, as shown in FIG. 4. The securement members 20 increase stent retention on the catheter system 5. By securing stent 28 to the catheter system 5 via the securement members 20, the longitudinal motion of the stent 28 is substantially eliminated during delivery.

In some embodiments, not every strut pair comprises protuberances. The strut pair 62 shown in FIG. 2 does not comprise protuberances. In FIG. 2, strut pairs 60 with protuberances 65 alternate with strut pairs 62, without protuberances. It is also possible that there are multiple strut pairs 62 placed between strut pairs 60 with protuberances 65. However, it may be desirable to have every strut pair comprise protuberances 65.

In some embodiments the stent may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto. The entirety or any portion(s) of the stent may include one or more therapeutic agents. A therapeutic agent may be a drug or other pharmaceutical product such as non-genetic agents, genetic agents, cellular material, etc. Some examples of suitable non-genetic therapeutic agents include but are not limited to: antithrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

In at least one embodiment, the catheter system 5 further comprises an expandable balloon 70, as shown in FIG. 1. In such an embodiment, the balloon 70 comprises the engagement region 25, upon which at least a portion of securement member 20 is secured. Also, as shown in FIG. 1, stent 28 is disposed about balloon 70 with main body 85. As depicted in FIG. 2, stent 28 is disposed such that securement members 20 are aligned between protuberances 65.

Figure 5:
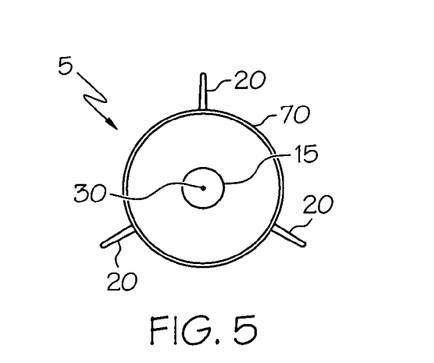
FIG. 5 is an end view of the catheter system shown in FIG. 1, in an expanded state.

Another advantageous embodiment of the invention includes a plurality of securement members. FIG. 1 depicts catheter system 5 with a plurality of securement members 20, positioned longitudinally along longitudinal axis 30 in rows 80, as well as circumferentially about the about the engagement region 25. FIG. 5 illustrates an end view of the catheter system of FIG. 1, further depicting the longitudinal and circumferential placement of the plurality of securement members 20. Although the catheter system 5 of both FIG. 1 and FIG. 5 depicts the plurality of securement members 20 extending longitudinally along longitudinal axis 30 as well extending circumferentially about the engagement region, one of ordinary skill in the art would recognize that a variety of different patterns of securement members placed on the exterior of the balloon may be desirable, including random placement. Patterns may include helical, spiral, or other placement.

Figure 6:
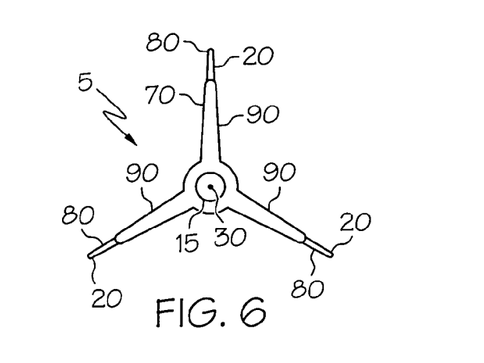
FIG. 6 is an end view of the catheter system shown in FIG. 1, comprising an unexpanded, folded balloon with securement members.
Figure 7:
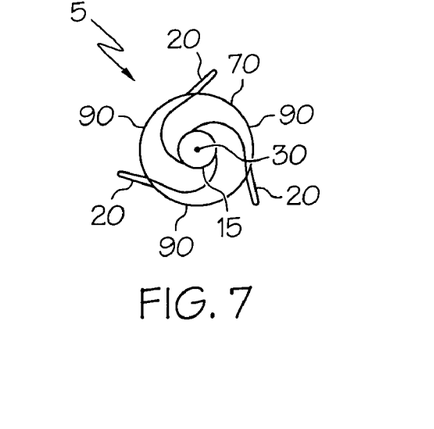
FIG. 7 is an end view of the catheter system shown in FIG. 1, comprising an unexpanded, folded balloon with securement members in a wrapped state.
Figure 8:
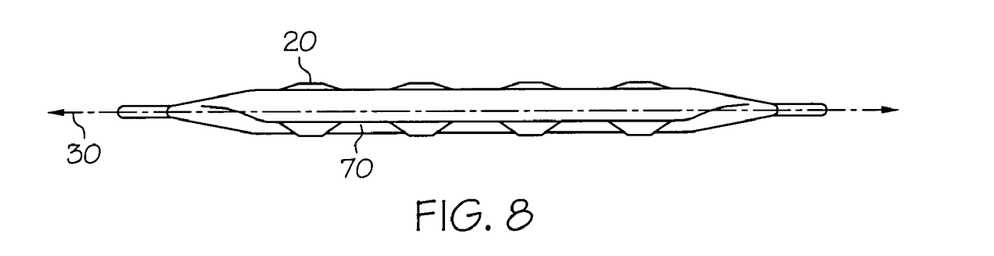
FIG. 8 is a side view of the catheter system shown in FIG. 7.

Referring now to FIG. 6, some embodiments of the invention include a balloon 70 which includes a plurality of folds 90 along balloon main body 85. The folds 90 extend along longitudinal axis 30, and securement members 20 are engaged to and along folds 90 in rows 80. FIG. 7 depicts the embodiment shown in FIG. 6 in a wrapped state. In the wrapped state, folds 90 of balloon 70 are circumferentially wrapped around longitudinal axis 30, thereby reducing the balloon's overall profile. This reduction in profile is depicted in FIG. 8, which shows a side view of balloon in a wrapped state. Although stent 28 is not depicted in FIG. 7, stent 28 is placed on balloon 70 in the wrapped state of FIG. 7. Once stent 28 is placed on the balloon 70 and crimped, securement members 20 engage with the protuberances 65, as shown in FIGS. 2-4. FIG. 5 depicts the balloon 70 of FIG. 7 in an unwrapped and expanded state, after stent 28 and balloon 70 have been delivered. After delivery, and as balloon 70 is inflated, protuberances 65 disengage from securement members 20, thereby allowing the release of stent 28 from balloon 70.

Figure 9:
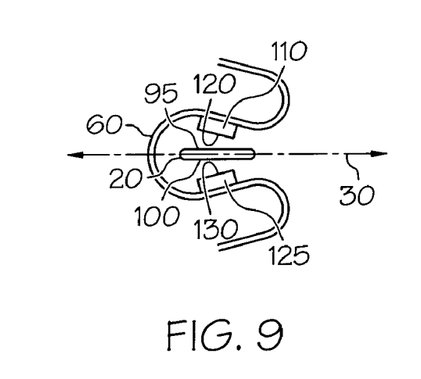
FIG. 9 is a top view of the portion of the stent shown in FIG. 3, with protuberances having surface areas substantially parallel to the catheter system's longitudinal axis.

In some embodiments, securement member 20 has surface areas (95 and 100) that are substantially parallel to the longitudinal axis 30, as shown in FIG. 9. FIG. 9 depicts a securement member 20 having a first surface area 95 and second surface area 100. Both first surface area 95 and second surface area 100 are substantially parallel to longitudinal axis 30. The strut pair 60 comprises a first protuberance 110, having a first surface 120, and a second protuberance 125, having a second surface 130. In an unexpanded state, first surface area 95 will engage first surface 120, and second surface area 100 will engage second surface 130, thereby securing the stent to the catheter.

Figure 10:
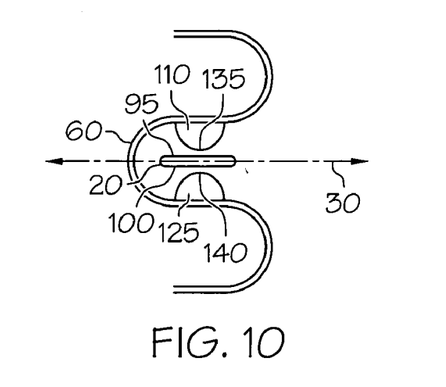
FIG. 10 is a top view of the portion of the stent shown in FIG. 3, with protuberances having convex regions to engage a securement member.

In another advantageous embodiment, both first protuberance 110 and second protuberance 125 comprise substantially convex regions, as depicted in FIG. 10. FIG. 10 shows first protuberance 110 having a first convex region 135 and second protuberance 125 having a second convex region 140. Also, FIG. 10 depicts securement member 20 having a first surface area 95 and second surface area 100, both surface areas being substantially parallel to longitudinal axis 30. In an unexpanded state, first convex region 135 will engage first surface area 95, and second convex region 140 will engage second surface area 100, thereby securing the stent to the catheter.

Figure 11:
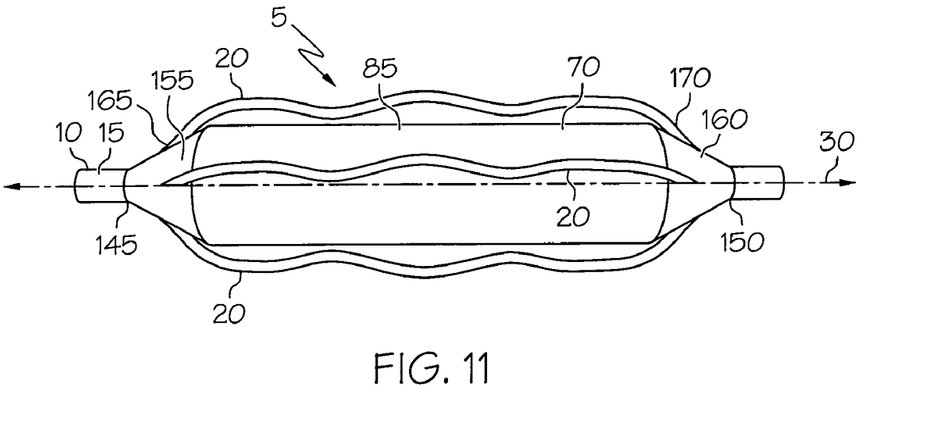
FIG. 11 is a side view of an embodiment of the invention, comprising securement members that extend from a first end tapered region to a second end tapered region.

In some embodiments of the present invention, the catheter system comprises a catheter having a catheter shaft, an expandable balloon, and at least one securement member engaged to the balloon, as shown in FIG. 11. In FIG. 11, a catheter system, shown generally at 5, comprises a catheter 10 with catheter shaft 15, and at least one securement member 20. Expandable balloon 70, disposed about catheter 10, has a first end 145, a second end 150, and a main body 85 therebetween. First end 145 and second end 150 are each engaged to catheter shaft 15. First end tapered region 155 is positioned between first end 145 and balloon main body 85; second end tapered region 160 is positioned between second end 150 and balloon main body 85. Securement member 20 is engaged to balloon 70. In one advantageous embodiment, at least one securement member 20 is engaged to one of either the first end tapered region 155 or second end tapered region 160.

In at least one embodiment, as shown in FIG. 11, securement member 20 has a first end 165 and a second end 170. First end 165 is engaged to first end tapered region 155 and second end 170 is engaged to second end tapered region 160. Some embodiments of the present invention comprise a plurality of securement members 20.

Figure 12:
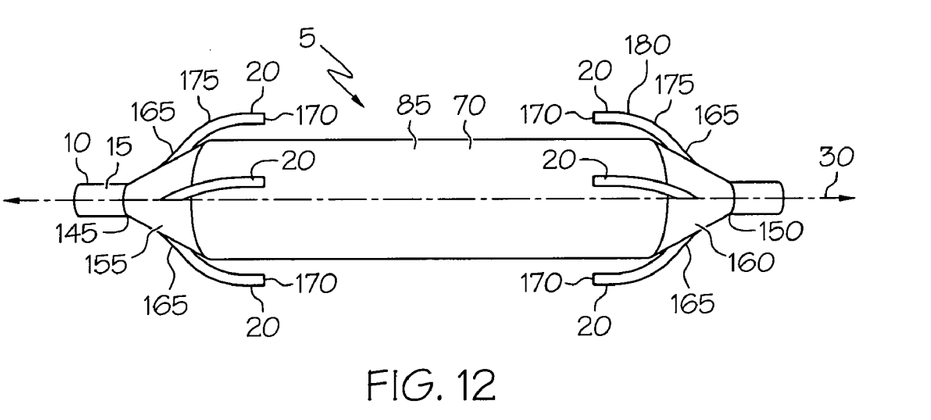
FIG. 12 is a side view of an embodiment of the invention, comprising securement members wherein only one end of a securement member is attached to an end tapered region.
Figure 13:
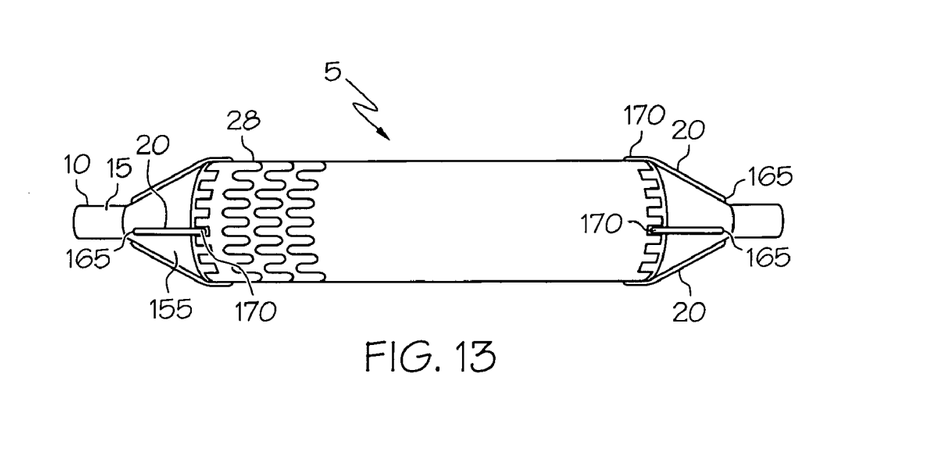
FIG. 13 is a side view of an embodiment of the invention shown in FIG. 12, further including a stent with securement members attached thereto.

In some embodiments of the present invention, as depicted in FIGS. 12 and 13, only the first end of the securement member is engaged to an end tapered region. FIG. 12 shows catheter system 5 prior to stent placement on the balloon 70. FIG. 13 shows the catheter system 5 of FIG. 12 after the stent has been placed on balloon 70, the stent being secured by the second end 170 of the securement member.

Figure 14:
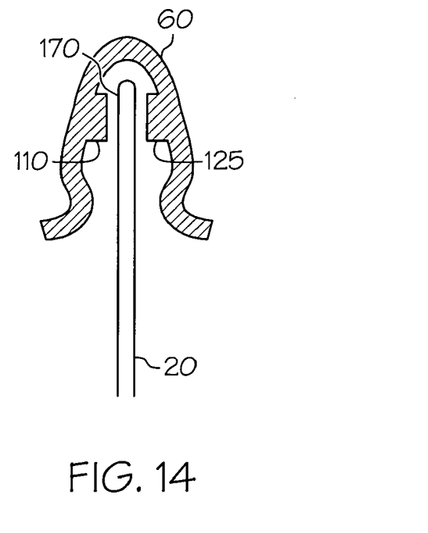
FIG. 14 is a top view of a portion of the stent of FIG. 13, shown with protuberances and in an expanded state.
Figure 15:
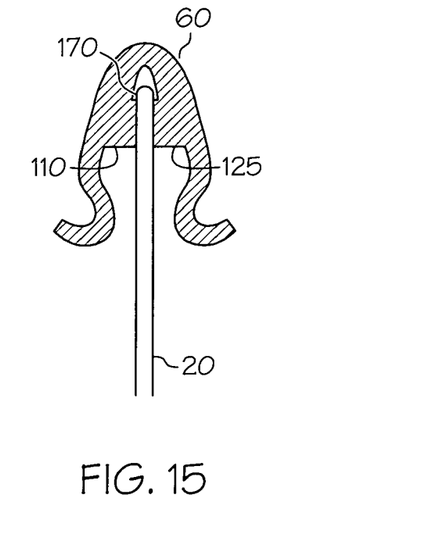
FIG. 15 is a top view of a portion of the stent of FIG. 13, shown with protuberances and in an unexpanded state and engaged to a securement member.
Figure 16:
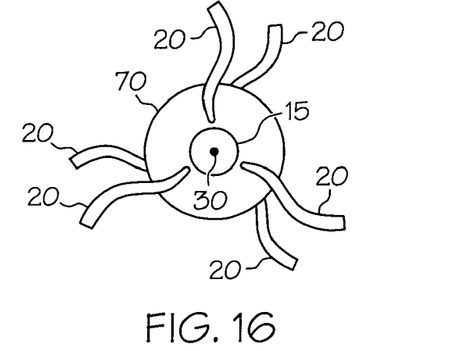
FIG. 16 is an end view of the embodiment shown in FIG. 12.

FIG. 12 depicts catheter system 5 with a plurality of securement members 20, each with first end 165 and second end 170. The first end 165 of each securement member 20 is engaged to one of either the first end tapered region 155 or second end tapered region 160. The second end 170 of securement member 20 is engaged to a stent 28 with first and second protuberances (110 and 125), as shown in FIGS. 13-15. FIG. 16 shows an end view of this embodiment. Although FIG. 12 depicts both a first plurality 175 of securement members 20 and a second plurality 180 of securement members 20, it may be desirable to have only one of either plurality; that is, having only one end of the stent secured may be desirable. It also may be desirable to have only a single securement member 20, rather than a plurality. In other embodiments, the securement members are engaged to the main body of the balloon, rather than the end tapered region. In alternate embodiments, the securement members are engaged to the catheter shaft itself. It may be desirable in other embodiments to include a combination of these features, whereby the securement members are engaged to any combination of the catheter shaft, the main body of the balloon, and the end tapered regions.

Figure 17:
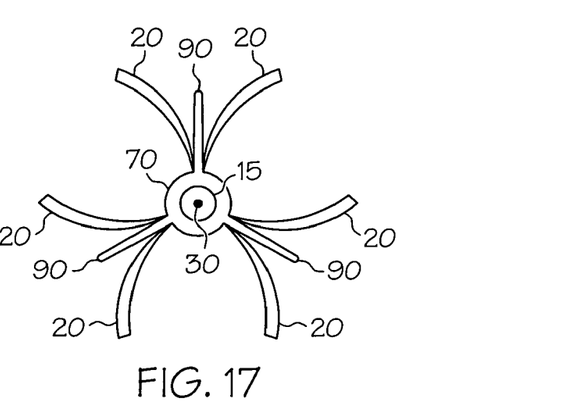
FIG. 17 is an end view of the embodiment shown in FIG. 12, with the balloon folded and in an unexpanded state.

In an advantageous embodiment, the present invention may include a balloon 70 with folds 90, as depicted in FIG. 17. This embodiment shows the catheter system in an unwrapped state. In the unwrapped state, folds 90 of balloon 70 extend longitudinally along longitudinal axis 30, with securement members 20 extending between the folds 90. In the wrapped state (not depicted), securement members 20 are engaged to a stent with protuberances, and the folds 90 are circumferentially wrapped around longitudinal axis 30, thereby reducing the balloon's overall profile.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A catheter system comprising:
 a catheter comprising a catheter shaft;
 an expandable balloon comprising an engagement region;
 a plurality of fin shaped securement members, each securement member having a first surface area and a second surface area, at least a portion of the securement members being engaged to the engagement region; and
 a stent having a longitudinal axis, an unexpanded configuration and an expanded configuration, the stent disposed about the catheter, the stent comprised of at least one undulating band extending circumferentially around the longitudinal axis, the at least one undulating band comprised of a plurality of interconnected strut members, each strut member having a length, the interconnected strut members forming a series of alternating peaks and valleys, two immediately adjacent strut members comprising a strut pair, the strut members of the strut pair comprising a first protuberance and a second protuberance, the first and second protuberances being positioned along the length of the respective strut member, between a peak and a valley, the first and second protuberances being substantially circumferentially opposed to one another, wherein the stent comprises a plurality of strut pairs;
 each first surface area of the securement member being grippedly engaged by the first protuberance in an unexpanded configuration and each second surface area of the securement member being grippedly engaged by the second protuberance in an unexpanded configuration, the plurality of securement members being disengaged from the protuberances in an expanded configuration, wherein the securement members extend outwardly from the surface of the balloon.

2. The catheter system of claim 1, wherein the plurality of securement members are positioned circumferentially about the balloon.

3. The catheter system of claim 1, wherein the plurality of securement members are positioned longitudinally along the balloon in at least one row.

4. The catheter system of claim 3 wherein the expandable balloon comprises a main body, the main body of the expandable balloon comprising a plurality of folds, the plurality of folds extending longitudinally, the catheter system further comprising at least two rows of securement members, each row of securement members being engaged to a fold.

5. The catheter system of claim 1, wherein the plurality of securement members are positioned circumferentially and longitudinally about the expandable balloon.

6. The catheter system of claim 1 wherein each of said surface areas is substantially parallel with the longitudinal axis, at least a portion of each of said surface areas positioned between the substantially opposing protuberances.

7. The catheter system of claim 6 wherein each of said surfaces is substantially parallel with the longitudinal axis.

8. The catheter system of claim 6 wherein the first protuberance has a first convex region and the second protuberance has a second convex region, at least a portion of the first convex region being engaged to the first surface area of the securement member, at least a portion of the second convex region being engaged to the second surface area of the securement member.

9. A catheter system comprising:
 a catheter comprising a catheter shaft;
 an expandable balloon comprising an engagement region;
 at least one fin shaped securement member; and
 a stent having a longitudinal axis, an unexpanded configuration and an expanded configuration, the stent comprised of at least one undulating band extending circumferentially around the longitudinal axis, the at least one undulating band comprised of a plurality of interconnected strut members, each strut member having a length, the interconnected strut members forming a series of alternating peaks and valleys, two immediately adjacent strut members comprising a strut pair, each strut member of the strut pair comprising at least one protuberance, the at least one protuberance being positioned along the length of the strut member, between a peak and a valley, the protuberances being substantially circumferentially opposed to one another, the at least one securement member being engaged by at least two protuberances in an unexpanded configuration and disengaged from the protuberances in an expanded configuration.

10. A catheter system comprising:
 a catheter comprising a catheter shaft;

an expandable balloon having an unexpanded configuration and an expanded configuration, the expandable balloon disposed about the catheter, the expandable balloon comprising a first end, a second end, and a main body therebetween, the first end and second end engaged to the catheter shaft, a first end tapered region positioned between the first end of the balloon and the main body of the balloon, and a second end tapered region positioned between the second end of the balloon and the main body of the balloon;

a stent having a longitudinal axis, the stent disposed about the balloon, the stent comprised of at least one undulating band extending circumferentially around the longitudinal axis, the at least one undulating band comprised of a plurality of interconnected strut members, each strut member having a length, the interconnected strut members forming a series of alternating peaks and valleys, two immediately adjacent strut members comprising a strut pair, each strut member of the strut pair comprising at least one protuberance, the at least one protuberance being positioned along the length of the strut member, between a peak and a valley, the protuberances being substantially circumferentially opposed to one another; and a plurality of securement members engaged to the balloon, wherein each securement member is secured between the substantially circumferentially opposed protuberances of a strut pair and engaged thereto in an unexpanded configuration and disengaged from the protuberances in an expanded configuration.

11. The system of claim 10 wherein at least one of the plurality of securement members is engaged to one of said end tapered regions.

12. The system of claim 10 wherein at least one of the plurality of securement members has a first end and a second end, the first end being directly engaged to the first end tapered region and the second end being directly engaged to the second end tapered region.

13. The system of claim 10, wherein each securement member has a first end and a second end, the first end of each of said plurality of securement members being engaged to one of said end tapered regions.

14. The system of claim 13 wherein the plurality of securement members comprises a first plurality of securement members and a second plurality of securement members, the first ends of the first plurality of securement members being engaged to the first end tapered region, the first ends of the second plurality of securement members being engaged to the second end tapered region.

15. The system of claim 10, wherein the main body of the balloon further comprises a plurality of folds, each fold extending along a longitudinal axis, the securement members extending between said folds.

* * * * *